(12) United States Patent
Ono

(10) Patent No.: US 7,331,673 B2
(45) Date of Patent: Feb. 19, 2008

(54) OPHTHALMIC PHOTOGRAPHY APPARATUS AND OPHTHALMIC PHOTOGRAPHY METHOD

(75) Inventor: Shigeaki Ono, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 259 days.

(21) Appl. No.: 11/184,173

(22) Filed: Jul. 19, 2005

(65) Prior Publication Data
US 2006/0028618 A1    Feb. 9, 2006

(30) Foreign Application Priority Data
Jul. 20, 2004    (JP)    ............ 2004-211691

(51) Int. Cl.
*A61B 3/10*    (2006.01)
*A61B 3/14*    (2006.01)

(52) U.S. Cl. ............ 351/221; 351/206
(58) Field of Classification Search ........... 351/221
See application file for complete search history.

(56) References Cited

U.S. PATENT DOCUMENTS 6,158,864 A    12/2000    Masuda

2003/0071966 A1*    4/2003    Matsumoto ........ 351/206

FOREIGN PATENT DOCUMENTS

| JP | 4-352934 | 12/1992 |
|---|---|---|
| JP | 9-262211 | 10/1997 |
| JP | 10-234671 | 9/1998 |

\* cited by examiner

*Primary Examiner*—Alicia M Harrington
(74) *Attorney, Agent, or Firm*—Canon U.S.A. Inc I.P. Div

(57) ABSTRACT

An ophthalmic photography apparatus includes an illumination light source operable to illuminate an eye to be examined, a light-intensity adjusting unit operable to adjust a light intensity of the illumination light source, an illumination optical system guiding light from the illumination light source to the eye, a photography light source facilitating photographing a still image of the eye, an imaging device converting received light into an electrical signal, an amplifying section amplifying the electrical signal according to an amplification factor, a photography optical system guiding an image of the eye to the imaging device, and a driving section driving the light-intensity adjusting unit and the amplifying unit. The driving section drives the light-intensity adjusting unit or the amplifying unit according to a value related to the eye to be examined.

7 Claims, 8 Drawing Sheets

OPHTHALMIC PHOTOGRAPHY APPARATUS AND OPHTHALMIC PHOTOGRAPHY METHOD

BACKGROUND OF THE INVENTION

1. Field of the Invention

The present invention relates to ophthalmic photography apparatuses and ophthalmic photography methods for photographing eyes for examination.

2. Description of the Related Art

Ophthalmic photography apparatuses for acquiring an image of an eye to be examined through the use of an imaging device, such as a charge-coupled device (CCD), and then converting the acquired image into a video signal for the purpose of aligning, observing, and photographing the eye are described in, for example, Japanese Patent Laid-Open Nos. 9-262211 (corresponding to U.S. Pat. No. 6,158,864) and 10-234671.

These apparatuses are controlled so as to produce an optimal video signal from the image of the eye to be examined by electrically amplifying the signal output from the CCD.

Typically, these apparatuses have fixed control ranges of the parameters: light intensity of an illumination light source and the amplification factor of the image signal from the imaging device, where these parameters can be set to their respective maximum values.

Furthermore, ophthalmic photography apparatuses including a plurality of image-recording units and a limiting unit for limiting the upper-limit intensity of illumination light for each of the image-recording units are described in, for example, Japanese Patent Laid-Open No. 4-352934.

For fluorescein fundus angiography (or indocyanine green fundus angiography), it is difficult to determine the intensity of photographing light when attempting to record a fundus image through the use of a photography light source in the first-half stage of fluorescein fundus angiography (or indocyanine green fundus angiography) processing, particularly until an indocyanine green (or fluorescein sodium) fully circulates through the fundus blood vessels, due to a great change in the brightness of the fundus. To circumvent this drawback, a method for recording a fundus image by the use of only observation illumination light is desirable. With this method, however, the intensity of the observation light needs to be increased and the amplification factor of the video signal from the imaging device needs to be minimized in order to obtain a fundus image with a S/N ratio sufficiently high for diagnosis.

On the other hand, in the second-half stage of fluorescein fundus angiography (or indocyanine green fundus angiography) processing in which the indocyanine green (or fluorescein sodium) has fully circulated though the fundus blood vessels and fluorescence starts to disappear from the fundus blood vessels, it is relatively easy to determine the intensity of photographing light when attempting to record a fundus image through the use of the photography light source since the fundus does not exhibit a significant change in brightness. For this reason, in the second-half stage of fluorescein fundus angiography (or indocyanine green fundus angiography) processing in which fluorescence disappears from the fundus blood vessels and accordingly the fundus becomes dark, the use of photographing light, in addition to observation light, allows a fundus image with a high S/N ratio to be produced without having to set a very high amplification factor of the video signal from the imaging device. On the other hand, for the purpose of aligning the fundus, it is necessary to increase the intensity of observation light and to maximize the amplification factor of the video signal from the imaging device.

Thus, with the above-described known photography method, the observation illumination light needs to maintain the maximum light intensity allowed in the apparatus throughout the first-half and second-half stages of the fluorescein fundus angiography (or indocyanine green fundus angiography) processing. In other words, none of the above-described known ophthalmic photography apparatuses discloses the idea of changing the photography conditions, such as the light intensity of observation illumination light, depending on the status of the eye to be examined, such as whether the eye is in the first-half stage or second-half stage of fluorescein fundus angiography (or indocyanine green fundus angiography) processing, when the eye is to be photographed using a single image-recording unit.

Furthermore, a long-term examination with the maximum intensity of observation light causes the examined eye to receive high intensity observation light. This bothers the subject.

SUMMARY OF THE INVENTION

The present invention is directed to an ophthalmic photography apparatus which allows an eye to be photographed appropriately with a simple operation.

According one aspect of the present invention, an ophthalmic photography apparatus includes: an illumination light source operable to illuminate an eye to be examined; a light-intensity adjusting section operable to adjust a light intensity of the illumination light source; an illumination optical system guiding light from the illumination light source to the eye; a photography light source facilitating photographing a still image of the eye; an imaging device converting received light into an electrical signal; an amplifying section amplifying the electrical signal from the imaging device according to an amplification factor; a photography optical system guiding an image of the eye to be examined, illuminated by the illumination light source, to the imaging device; and a driving section driving the light-intensity adjusting unit and the amplifying unit. The driving section drives the light-intensity adjusting unit or the amplifying unit according to a value related to a state of the eye to be examined.

According to another aspect of the present invention, an ophthalmic photography method includes steps of: illuminating an eye to be examined with illumination light; adjusting a light intensity of the illumination light in the illuminating step; guiding the illumination light to the eye to be examined and converting an image of the illuminated eye to be examined into an electrical signal; amplifying the electrical signal according to an amplification factor; and adjusting the light intensity of the illumination light and the amplification factor. The light intensity of the illumination light or the amplification factor is adjusted according to a value related to a state of the eye to be examined.

According to still another aspect of the present invention, a control program stored on a recording medium causes a computer to execute the above-described ophthalmic photography method.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

First Embodiment

The present invention will now be described in detail with reference to the embodiments shown in FIGS. 1 to 9.

Figure 1:
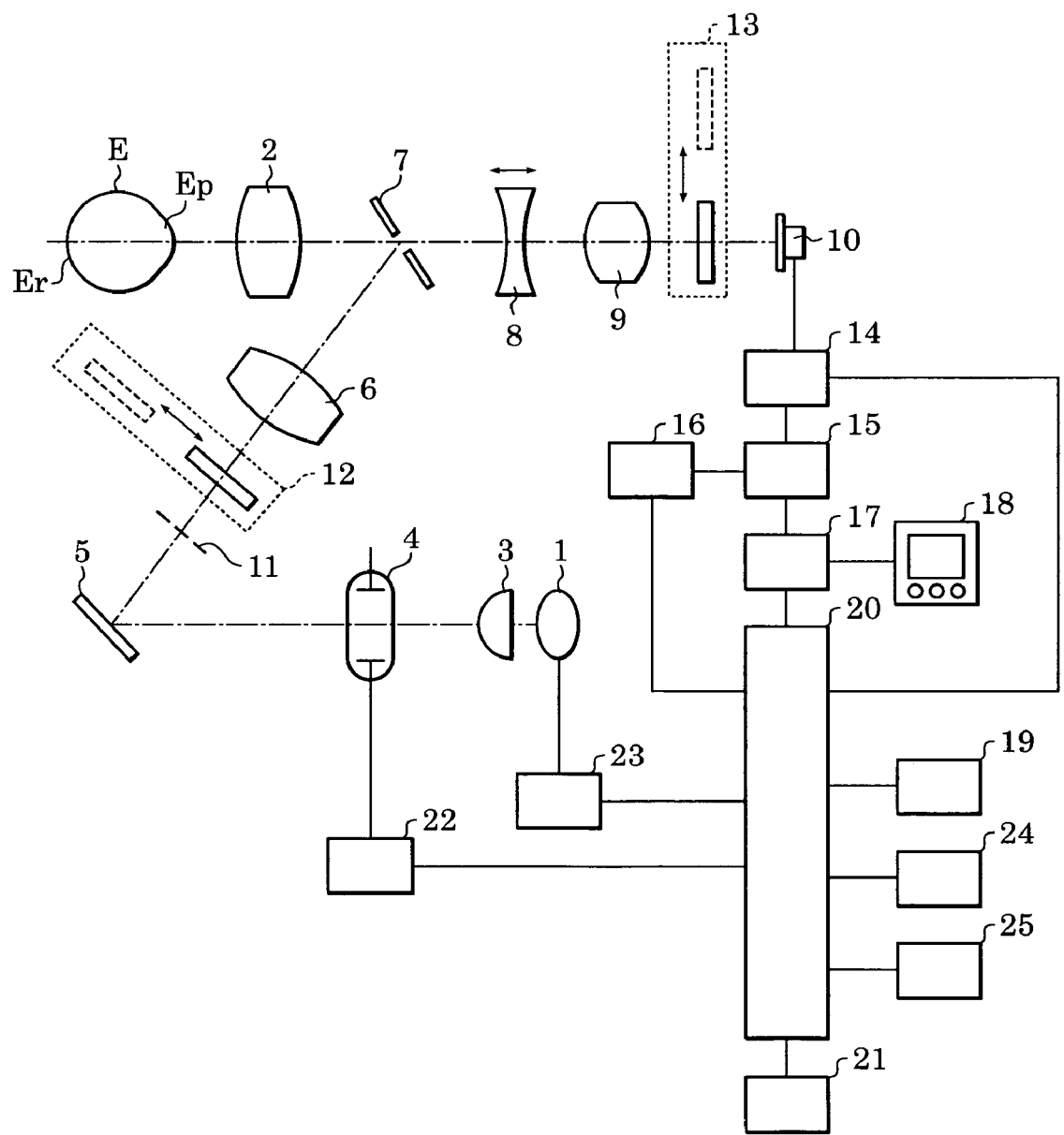
FIG. 1 is a block diagram depicting a fundus camera according to a first embodiment.

FIG. 1 is a block diagram depicting a fundus camera according to a first embodiment. A condenser lens 3, a photography light source 4, a mirror 5, an aperture 11 having a ring opening, a removable excitation filter for indocyanine green angiography 12, a relay lens 6, and a mirror 7 with a hole are arranged in series along the light path extending from an observation light source 1 to an objective lens 2. These members are included in a fundus photography optical system. The fundus photography optical system also includes a focusing lens 8, a photography lens 9, a removable barrier filter for indocyanine green angiography 13 for cutting excitation light and transmitting only fluorescence, and an imaging device 10, which are arranged on the light path in the transmission direction of the mirror 7 with a hole.

An accumulated-electric-charge reading section 14, an amplifying section 15, an image-signal processing section 17, and a system control section 20 are connected in series to the output of the imaging device 10.

The amplifying section 15 is connected to an amplification-factor control section 16, and the video signal is amplified by an amplification factor set by the amplification-factor control section 16.

A display section 18 is connected to the image-signal processing section 17. It is used to observe the fundus to be examined and to display the photographed image of the fundus. The image-signal processing section 17, an image-recording unit 19, a photography switch 21, a photography-light-source control section 22, an observation-light-source control section 23, a timer switch 24 for starting and stopping time keeping by a timer, and an observation-condition changing knob 25 for increasing and decreasing the light intensity of the observation light source 1 and increasing and decreasing the amplification factor of the amplifying section 15 are connected to the system control section 20.

A beam emitted from the observation light source 1 passes through the condenser lens 3 and the photography light source 4 and is then reflected at the mirror 5. The light reflected at the mirror 5 passes through the aperture 11 having a ring opening, the excitation filter for indocyanine green angiography 12, and the relay lens 6. The light is then reflected on an area near the mirror 7 with a hole and passes through the objective lens 2 and a pupil Ep of an eye E to be examined to illuminate a fundus Er. The image of the illuminated fundus passes through the pupil Ep of the eye E to be examined, the objective lens 2, the hole of the mirror 7 with a hole, the focusing lens 8, the projector lens 9, and the barrier filter for indocyanine green angiography 13, and is finally focused on the imaging device 10.

The imaging device 10 holds an accumulated electric charge resulting from photoelectric conversion. The accumulated-electric-charge reading section 14 carries out the sequential operations of reading out the accumulated electric charge and clearing the held electric charge. While performing these sequential operations, the accumulated-electric-charge reading section 14 outputs the read-out signal to the image-signal processing section 17 through the amplifying section 15. The image-signal processing section 17 carries out processing necessary for outputting the signal to the display section 18 where the signal is visualized on the display section 18 as an observation image at that time.

The operation of the system control section 20 during observation and photography will be described with reference to the flowchart shown in FIG. 2.

An operator carries out alignment while observing the video on the display section 18. During the observation, in step S1, the observation-light-source control section 23 is set so that the upper limit value of the control range of light intensity of the observation light source 1 is equal to about 70% of the maximum value. As a result, the observation-light-source control section 23 controls the light intensity of the observation light source 1 in the range from 0% to 70% of the maximum value. Furthermore, in step S2, the amplification-factor control section 16 is set so that the upper limit value of the control range of the amplification factor of the amplifying section 15 is equal to the maximum value. As a result, the amplification-factor control section 16 controls the amplification factor of the amplifying section 15 in the range from 0% to 100% of the maximum value.

In step S3, observation-condition-changing-knob processing is carried out. Details of observation-condition-changing-knob processing will be described below.

After alignment is achieved, the operator presses the timer switch 24 upon the start of intravenous injection into the subject. If the system control section 20 detects the operation of the timer switch 24 in step S4, it starts time keeping with the timer in step S5.

In step S6, it is determined whether a predetermined period of time has elapsed since the start of time keeping with the timer. According to this embodiment, it is determined whether a time of 90 seconds has passed. Before the time of 90 seconds passes, the observation-light-source control section 23 is set so that the upper limit value of the control range of the light-intensity of the observation light source 1 is equal to the maximum value in step S7. As a result, the observation-light-source control section 23 controls the light intensity of the observation light source 1 in the range from 0% to 100% of the maximum value, as indicated by arrow (a) of FIG. 3. Furthermore, in step S8, the amplification-factor control section 16 is set so that the upper limit value of the control range of the amplification factor of the amplifying section 15 is equal to 70% of the maximum value. As a result, the amplification-factor control section 16 controls the amplification factor of the amplifying section 15 in the range from 0% to 70% of the maximum value, as indicated by arrow (b) of FIG. 3.

If the system control section 20 determines in step S4 that there is no input from the timer switch 24, the flow returns to step S3, where the system control section 20 monitors for an input from the timer switch 24 while carrying out observation-condition-changing-knob processing.

In step S9, if the operator presses the photography switch 21, the system control section 20 detects an input from the photography switch 21. In step S10, the system control section 20 acquires an image from the image-signal processing section 17 without illuminating the photography light source 4 and saves the acquired image in the image-recording unit 19. In this example, the image-recording unit 19 is a recording medium such as a hard disk, a CD-R/RW, a DVD-RAM, a DVD-R/RW, or a semiconductor memory.

In step S11, if the operator turns the observation-condition changing knob 25, the system control section 20 carries out observation-condition-changing-knob processing.

In observation-condition-changing-knob processing, if a change in the observation-condition changing knob 25 is detected in step S20, the amount of change in the observation-condition changing knob 25 is reported to the observation-light-source control section 23 in step S21. In response, the observation-light-source control section 23 controls the light intensity of the observation light source 1 in the specified range. Furthermore, in step S22 the amount of change in the observation-condition changing knob 25 is reported to the amplification-factor control section 16, so that the amplification-factor control section 16 controls the amplification factor of the amplifying section 15 in the specified range.

If it is determined in step S6 that the predetermined time of 90 seconds has elapsed since the start of time keeping with the timer, the observation-light-source control section 23 is set in step S14 so that the upper limit value of the control range of the light-intensity of the observation light source 1 is equal to 70% of the maximum value. As a result, the observation-light-source control section 23 controls the light intensity of the observation light source 1 in the range from 0% to 70% of the maximum value, as indicated with arrow (c) in FIG. 3. Furthermore, in step S15, the amplification-factor control section 16 is set so that the upper limit value of the control range of the amplification factor of the amplifying section 15 is equal to the maximum value. As a result, the amplification-factor control section 16 controls the amplification factor of the amplifying section 15 in the range from 0% to 100% of the maximum value, as indicated with arrow (d) in FIG. 3.

In step S16, if the operator presses the photography switch 21, the system control section 20 detects an input from the photography switch 21. In this case, in step S17 the amplification factor of the amplifying section 15 is set to a value for photography where the photography light source 4 is used.

Figure 4:
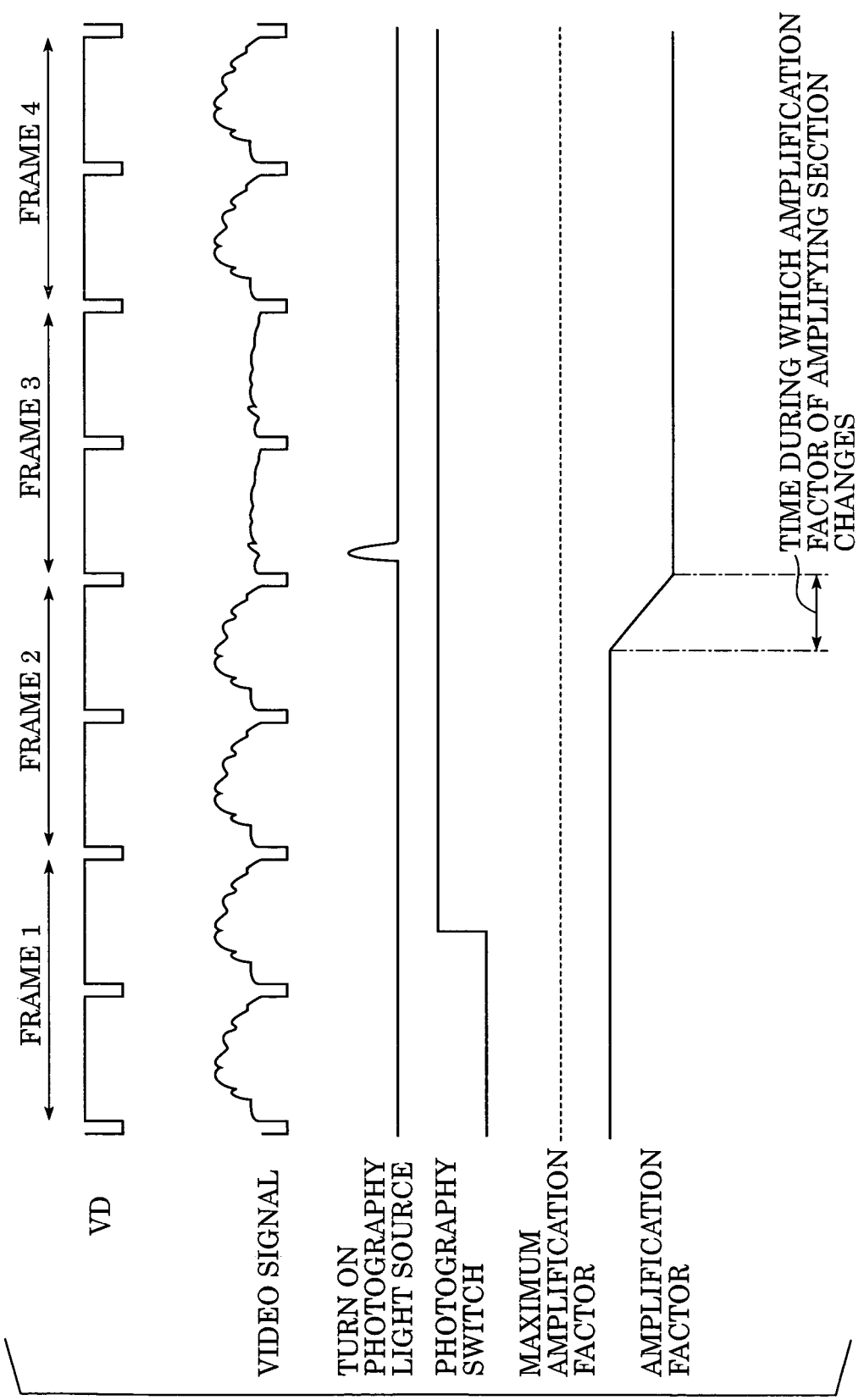
FIG. 4 is a photography timing diagram when light is emitted from a photography light source, according to the first embodiment.

In step S18, as shown in FIG. 4, the system control section 20 issues a flash-firing instruction to the photography-light-source control section 22 in synchronization with the vertical synchronizing signal. In response, the photography-light-source control section 22 emits light from the photography light source 4.

The beam emitted from the photography light source 4 carries a fundus image of the eye E to be examined to the imaging device 10, which then accumulates and holds an electric charge resulting from photoelectric conversion. The accumulated electric charge is read out in the accumulated-electric-charge reading section 14. The read-out video signal is amplified in the amplifying section 15, is converted into a digital signal by the A/D converter (not shown in the figure) through the image-signal processing section 17, and is input to the system control section 20. The converted digital video signal is recorded on the image-recording unit 19. In step S19, the amplification factor of the amplifying section 15 is set to a value for observation.

When the series of photography processes is completed, the operator presses the timer switch 24. When the system control section 20 detects an input of the timer switch 24 in step S12, time keeping by the timer ends in step S13 and the flow returns to step S1. This completes the photography processing for one patient.

Second Embodiment

The operation of the system control section 20 during observation and photography according to a second embodiment will now be described with reference to the flowchart shown in FIG. 5.

Figure 2:
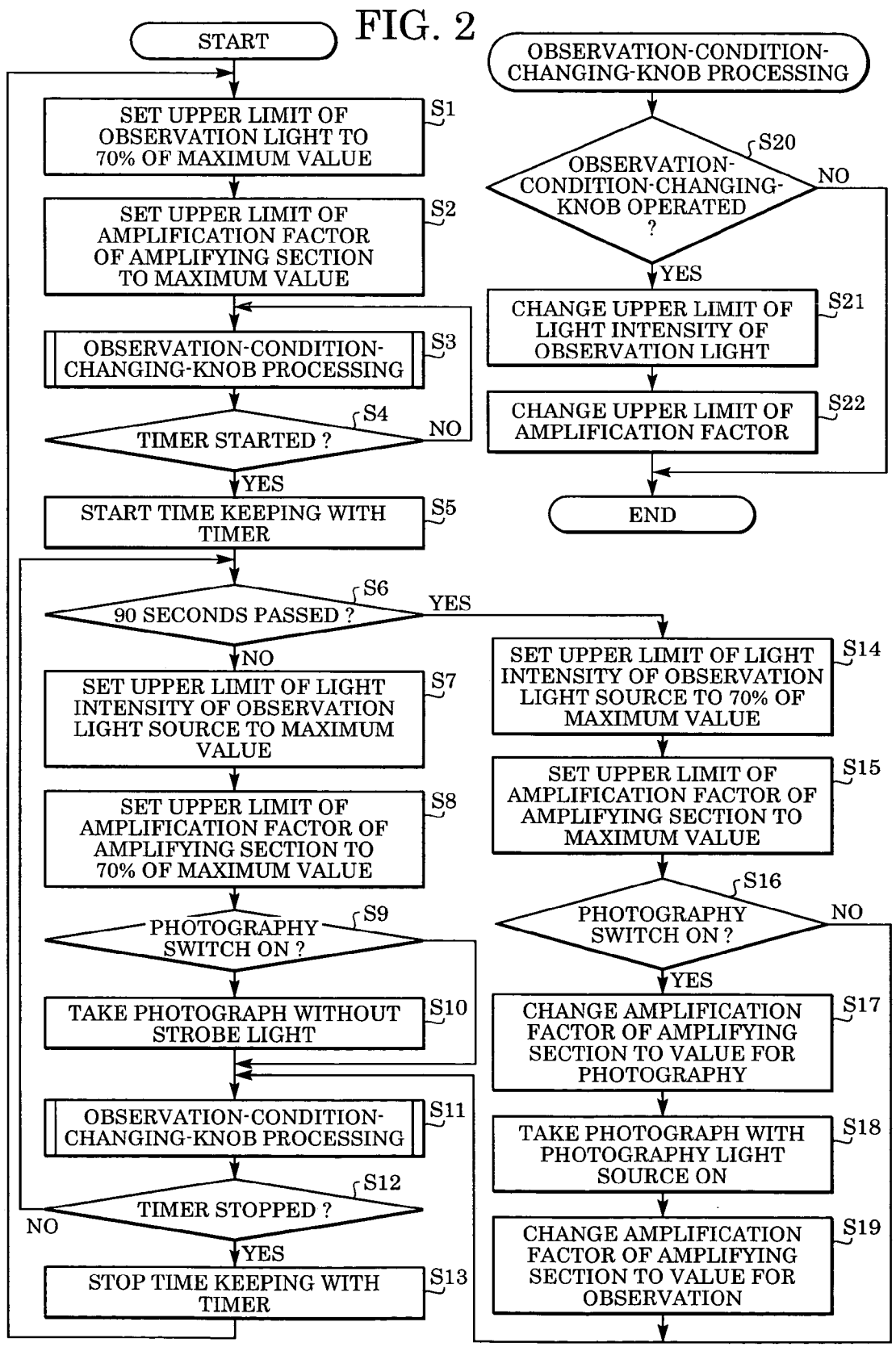
FIG. 2 is a flowchart illustrating the operation of a system control section according to the first embodiment.
Figure 3:
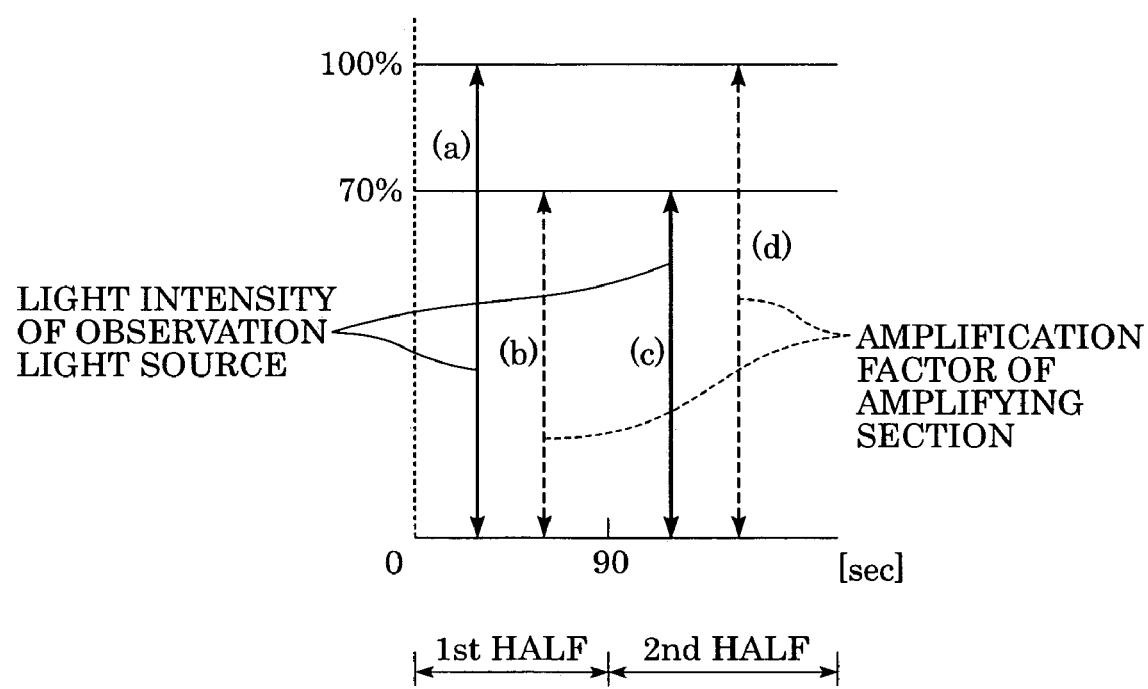
FIG. 3 is a diagram depicting the control ranges of an observation-light-source control section and an amplification-factor control section.
Figure 5:
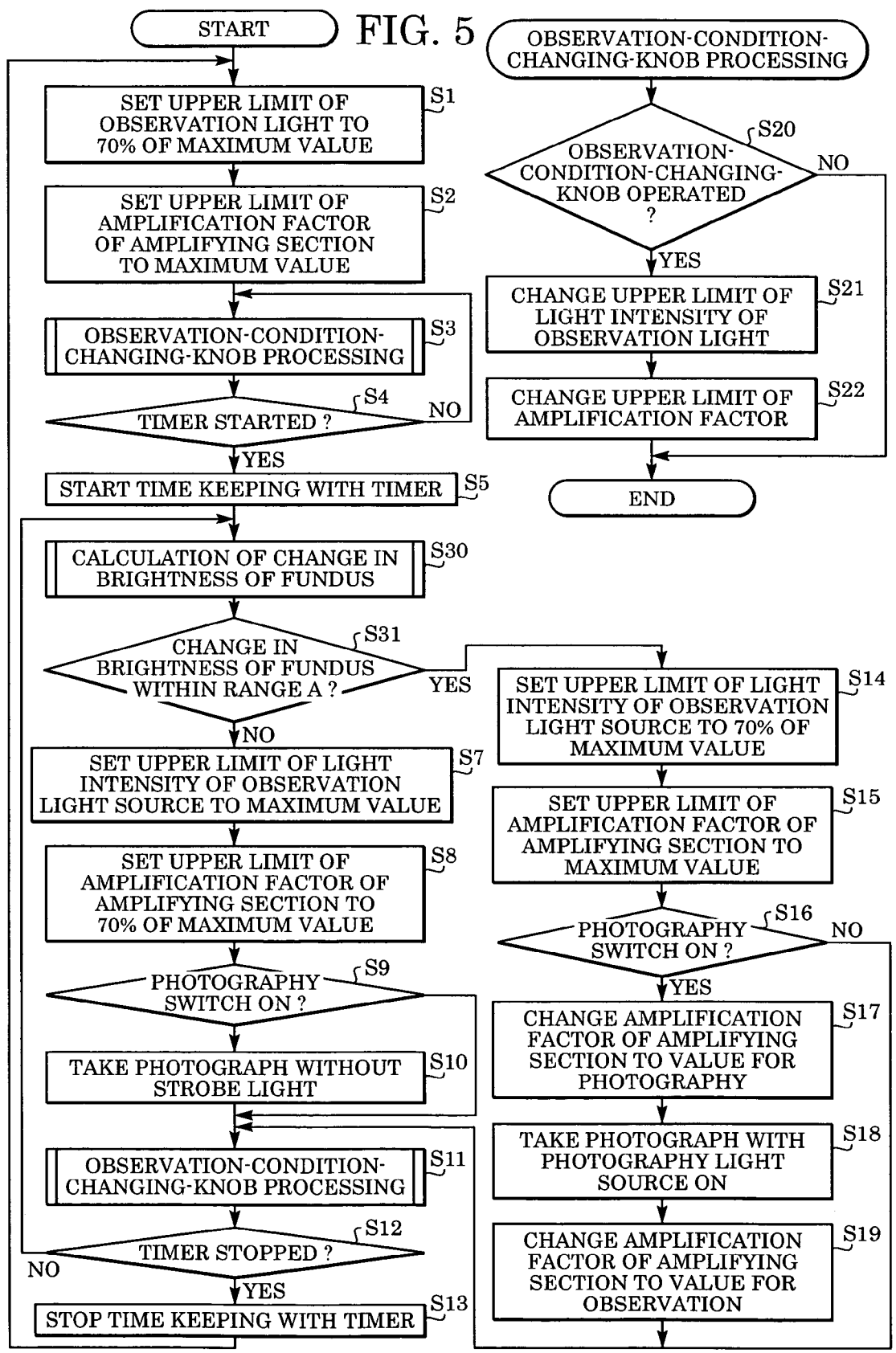
FIG. 5 is a flowchart illustrating the operation of the system control section according to a second embodiment.
Figure 6:
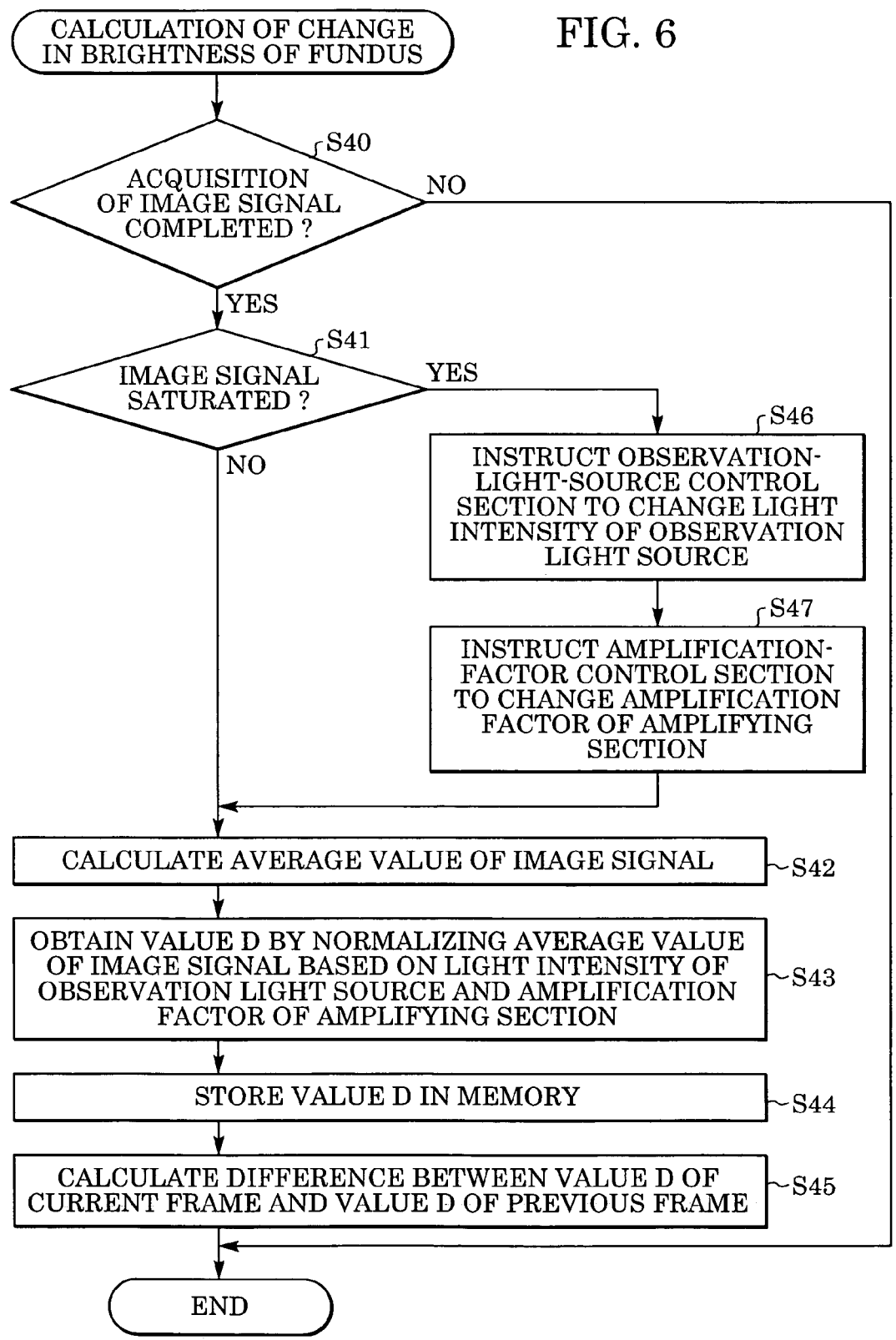
FIG. 6 is a flowchart applied when the system control section calculates a change in brightness of a fundus to be examined according to the second embodiment.

The flowchart in FIG. 5 differs from that shown in FIG. 2 in that the flowchart in FIG. 5 includes additional steps S30 and S31 in place of step S6 in FIG. 2.

In step S30, the system control section 20 calculates the change in brightness of the fundus to be examined. This calculation method will be described in detail with reference to the flowchart shown in FIG. 6.

A fundus image of the eye E to be examined is focused onto the imaging device 10, and an electric charge is accumulated and held as a result of photoelectric conversion. In the accumulated-electric-charge reading section 14, the accumulated electric charge is read out. The read-out video signal is amplified by the amplifying section 15, is converted into a digital signal by the A/D converter (not shown in the figure) through the image-signal processing section 17, and is input to the system control section 20, one frame at a time, as an image signal.

If it is determined in step S40 that the image signal has been input to the system control section 20, the acquired image signal is checked for saturation in step S41. If it is determined that the image signal is not saturated in step S41, the flow proceeds to step S42, where the average value of each frame in the image signal is obtained. Furthermore, in step S43, the average value is normalized (as a value D) based on the light intensity of the observation light source 1 and the amplification factor of the amplifying section 15. The change in the normalized value D over time is shown by curve (a) in FIG. 7. In step S44, the value D is stored in memory.

In addition, the system control section 20 calculates the difference in the value D between the current frame and the previous frame (step S45). The difference between the value D of the current frame and the value D of the previous frame is plotted in the time domain, as shown by curve (b) in FIG. 7. As this curve approaches 0, the fundus to be examined is subjected to a smaller change in brightness. For this reason, in step S31 of the flowchart shown in FIG. 5, the system control section 20 determines that the indocyanine green has fully circulated through the fundus blood vessels when the curve (b) of FIG. 7 falls in range A, and then causes the flow to proceed to step S14. The operation in step S14 and the subsequent operation are the same as in the first embodiment. If the curve (b) of FIG. 7 does not fall in range A in step S31, the system control section 20 determines that circulation of the indocyanine green in the fundus blood vessels is still in progress, and causes the flow to proceed to step S7. The operation in step S7 and the subsequent operation are the same as in the first embodiment.

At this time, while monitoring the level of the input image signal, the system control section 20 automatically controls the light intensity of the observation light source 1 in the set control range through the observation-light-source control section 23 and the amplification factor of the amplifying section 15 in the set control range through the amplification-factor control section 16 to prevent the image signal from saturating. In step S41 of the flowchart shown in FIG. 6, if it is determined that the acquired image signal is saturated, the flow proceeds to step S46, where the observation-light-source control section 23 is instructed to change the light intensity of the observation light source 1. Furthermore, the flow proceeds to step S47, where the amplification-factor control section 16 is instructed to change the amplification factor of the amplifying section 15.

Figure 7:
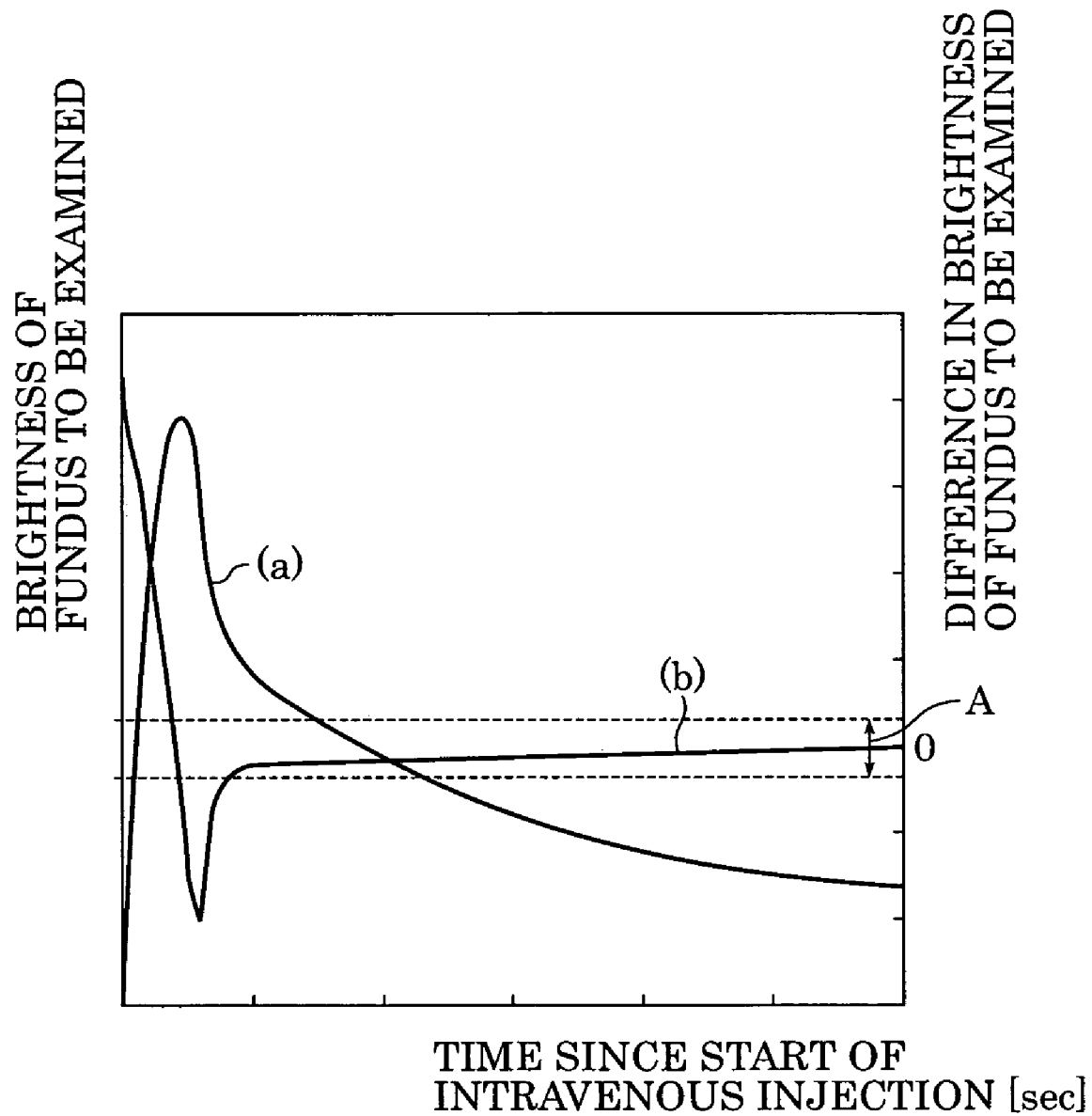
FIG. 7 is a diagram depicting changes in the brightness and brightness difference of a fundus over time.
Figure 8:
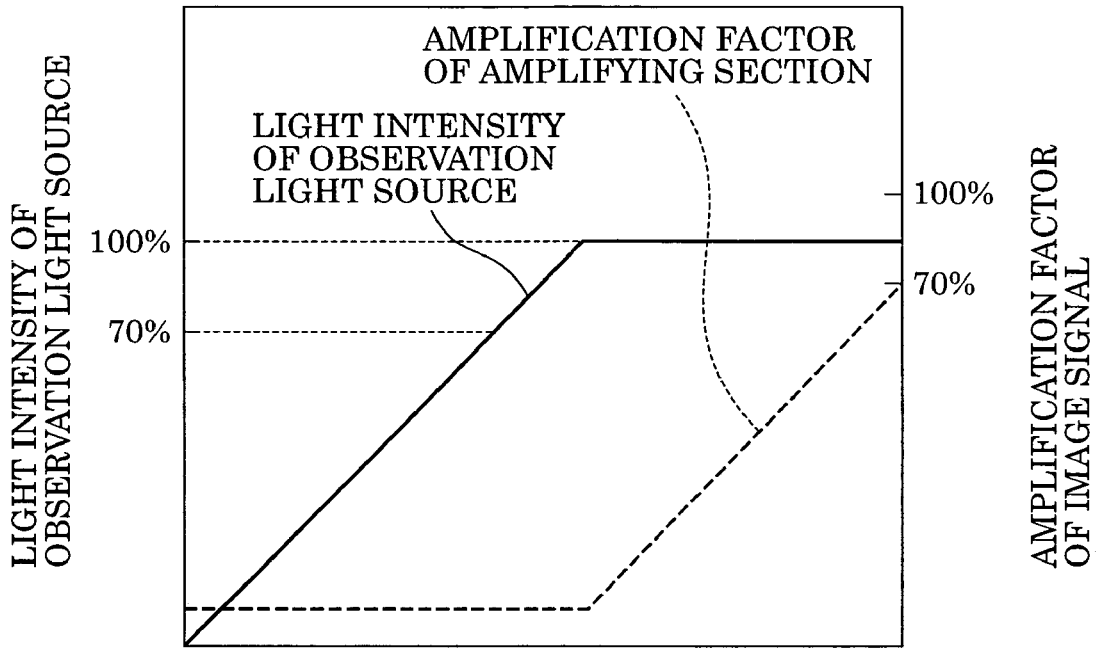
FIG. 8 is a diagram depicting a method for controlling the light intensity of an observation light source and the amplification factor of an amplifying section in the first-half stage of indocyanine green fundus angiography processing, according to the second embodiment.
Figure 9:
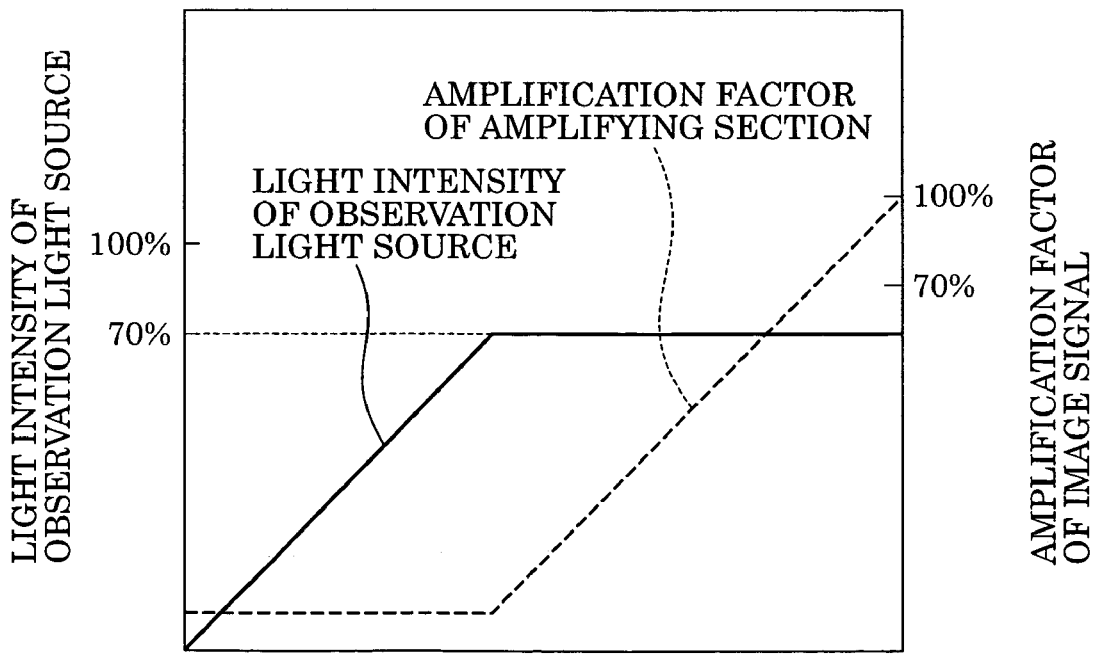
FIG. 9 is a diagram depicting a method for controlling the light intensity of the observation light source and the amplification factor of the amplifying section in the second-half stage of indocyanine green fundus angiography processing, according to the second embodiment.

FIG. 8 is a diagram depicting a method for controlling the light intensity of the observation light source 1 and the amplification factor of the amplifying section 15 in a case where the difference in the normalized value D is not within range A of FIG. 7. FIG. 9 is a diagram depicting a method for controlling the light intensity of the observation light source 1 and the amplification factor of the amplifying section 15 in a case where the difference in the normalized value D is within range A of FIG. 7.

Control is made such that the light intensity of the observation light source 1 is changed up to the upper limit value, and that after the light intensity of the observation light source 1 has reached the upper limit value, the amplification factor of the amplifying section 15 is changed up to the upper limit value.

The upper limit value of the light intensity of the illumination light source is the maximum value and the upper limit value of the amplification factor of the video signal output from the imaging device is below the maximum value before a predetermined period of time elapses after the start of indocyanine green fundus angiography. Therefore, even in the first-half stage of indocyanine green fundus angiography processing where the change in fluorescence from the eye to be examined is intense, a fundus image with a superior S/N ratio can be photographed with an appropriate light intensity, without having to use a strobe light. Furthermore, after the predetermined period has elapsed, the upper limit value of the light intensity of the illumination light source is below the maximum value, and the decreased intensity is compensated for with the amplification factor of the video signal output from the imaging device. This leads to an extended life span of the illumination light source and less discomfort to the subject.

As described above, the present invention allows an eye to be photographed appropriately with a simple operation.

Other Embodiments

The present invention can also be achieved by providing a computer in an apparatus or a system connected to devices so as to control the devices to achieve the function of the first embodiment with software program code for performing the functions of the foregoing embodiments (e.g., the functions achieved according to the flowcharts in FIGS. 2, 5, and 6) and then causing the computer (e.g., a CPU or MPU) of the system or apparatus to operate the devices according to the stored program.

In this case, the program code itself of the above-described software achieves the functions of the above-described embodiments. Thus, the program code itself and means for supplying a computer with the program code, such as a storage medium that records the program code, are included in the present invention.

A storage medium storing such program code includes a Floppy® Disk, a hard disk, an optical disk, a magneto-optical disk, a CD-ROM, a magnetic tape, a non-volatile memory card, and a ROM.

As described above, the functions of the above-described embodiments are achieved with the execution of the supplied program code read by the computer. In addition, the functions of the above-described embodiments may also be achieved by the operating system (OS) or other application software running on the computer that performs all or part of the processing according to the commands of the program code.

Furthermore, the functions of the above-described embodiments may also be achieved such that the supplied program code is written to a memory provided in an expansion card disposed in the computer or an expansion unit connected to the computer, and then, for example, the CPU provided on the expansion card or the expansion unit performs all or part of the processing based on commands in the program code.

While the present invention has been described with reference to exemplary embodiments, it is to be understood that the invention is not limited to the disclosed embodiments. The scope of the following claims is to be accorded the broadest interpretation so as to encompass all modifications, equivalent structures and functions.

This application claims priority from Japanese Patent Application No. 2004-211691 filed Jul. 20, 2004, which is hereby incorporated by reference herein in its entirety.

What is claimed is:

1. An ophthalmic photography apparatus comprising:
an illumination light source operable to illuminate an eye to be examined of a subject;
a light-intensity adjusting section operable to adjust a light intensity of the illumination light source;
a strobe emitting stroboscopic light;
an imaging device converting received light into an electrical signal;
an amplifying section amplifying the electrical signal from the imaging device according to an amplification factor;
a photography optical system guiding an image of the eye to the imaging device; and
a driving section controlling the illumination light source, the strobe, and the imaging device,
wherein the driving section photographs a still image by using only the illumination light source at a first time interval and photographs a still image by using the strobe at a second time interval after the first time interval passes, and
wherein the driving section sets an upper limit of the light intensity emitted by the illumination light source at the second time interval to exceed an upper limit of the light intensity emitted by the illumination light source at the first time interval.

2. The ophthalmic photography apparatus according to claim 1, further comprising a timer determining the first time interval and the second time interval.

3. The ophthalmic photography apparatus according to claim 2, wherein a beginning point of the first time interval is based on a start of an intravenous injection of the indocyanine green into the subject.

4. The ophthalmic photography apparatus according to claim 1, further comprising a calculating section calculating a change in the electrical signal from the imaging device over time, which corresponds to a change in brightness of the eye over time,
    wherein the driving section drives responsive to the change in the electrical signal from the imaging device over time calculated by the calculating section.

5. The ophthalmic photography apparatus according to claim 1, further comprising an amplifying section amplifying the electrical signal from the imaging device according to an amplification factor, wherein the amplifying section sets an upper limit of the amplification factor of the amplifying section at the first time interval to be lower than an upper limit of the amplification factor of the amplifying section at the second time interval.

6. An ophthalmic photography method comprising steps of:
    illuminating an eye to be examined with illumination light;
    adjusting a light intensity of the illumination light in the illuminating step; and
    photographing by guiding the illumination light to the eye to be examined and converting an image of the illuminated eye to be examined into an electrical signal,
    wherein an upper limit of the light intensity of the illumination light in the illuminating step is changed according to a start of an intravenous injection of a fluorescent agent into a subject.

7. A control program stored on a recording medium for causing a computer to execute the ophthalmic photography method according to claim 6.

* * * * *